United States Patent [19]

Koenitzer

[11] Patent Number: 4,929,358
[45] Date of Patent: May 29, 1990

[54] POLYURETHANE-IMIDE MEMBRANES AND THEIR USE FOR THE SEPARATION OF AROMATICS FROM NON-AROMATICS

[75] Inventor: Bernd A. Koenitzer, Clearwater, Canada

[73] Assignee: Exxon Research and Engineering Company, Florham Park, N.J.

[21] Appl. No.: 391,068

[22] Filed: Aug. 9, 1989

[51] Int. Cl.$^5$ ............................................. B01D 13/00
[52] U.S. Cl. ..................................... 210/640; 210/644; 210/651; 210/500.39
[58] Field of Search ............ 210/644, 640, 651, 500.39

[56] References Cited

U.S. PATENT DOCUMENTS 4,474,858  10/1984  Makino et al. ............. 210/500.39 X
4,802,987  2/1989   Black ................................... 210/640

Primary Examiner—Frank Spear
Attorney, Agent, or Firm—Joseph J. Allocca

[57] ABSTRACT

Aromatics are separated from non-aromatics by permeation of the aromatic through a polyurethane-imide membrane. Permeation is conducted under pervaporation, perstraction, reverse osmosis, or dialysis conditions. The membrane is a polyurethane-imide membrane made using polyurethane-imide copolymers which are made by end capping a polyol with a polyisocyanate and then chain extending by reaction with an anhydride.

10 Claims, No Drawings

POLYURETHANE-IMIDE MEMBRANES AND THEIR USE FOR THE SEPARATION OF AROMATICS FROM NON-AROMATICS

BRIEF DESCRIPTION OF THE INVENTION

Polyurethane-imide membranes made from polyurethane-imide copolymer produced by end capping a polyol with a polyisocyanate followed by chain extending by reaction with a polyanhydride has been found to be effective, high temperature stable membranes for separating aromatic hydrocarbons from non-aromatic hydrocarbons. Separation is performed under reverse osmosis, perstraction, pervaporation, dialysis condition, preferably perstraction or pervaporation, most preferably pervaporation. The polyurethane-imide membranes can be used at high temperatures without deterioration. Temperatures on the order of 140° C. and higher can be employed with no significant loss of selectivity.

BACKGROUND OF THE INVENTION

The use of membranes to separate aromatics from saturates has long been pursued by the scientific and industrial community and is the subject of numerous patents.

U.S. Pat. No. 3,370,102 describes a general process for separating a feed into a permeate stream and a retentate stream and utilizes a sweep liquid to remove the permeate from the face of the membrane to thereby maintain the concentration gradient driving force. The process can be used to separate a wide variety of mixtures including various petroleum fractions, naphthas, oils, hydrocarbon mixtures. Expressly recited is the separation of aromatics from kerosene.

U.S. Pat. No. 2,958,656 teaches the separation of hydrocarbons by type, i.e. aromatic, unsaturated, saturated, by permeating a portion of the mixture through a non-porous cellulose ether membrane and removing permeate from the permeate side of the membrane using a sweep gas or liquid. Feeds include hydrocarbon mixtures, naphtha (including virgin naphtha, naphtha from thermal or catalytic cracking, etc.).

U.S. Pat. No. 2,930,754 teaches a method for separating hydrocarbons e.g. aromatic and/or olefins from gasoline boiling range mixtures, by the selective permeation of the aromatic through certain cellulose ester non-porous membranes. The permeated hydrocarbons are continuously removed from the permeate zone using a sweep gas or liquid.

U.S. Pat. No. 4,115,465 teaches the use of polyurethane membranes to selectively separate aromatics from saturates via pervaporation.

Japanese application 38478/65 describes an imide bond containing polyurethane elastomer prepared by casting an isocyanate with a tetracarboxylic acid dianhydride or acid anhydride by chain propagation of a prepolymer having terminal isocyanate groups derived from the treatment of a polyglycol with an organic di-isocyanate The polymer, made in a solution, can be spun or made into transparent yellow films.

Japanese application 19134/65 teaches the preparation of polyimide urethane copolymers by the reaction of a tetracarboxylic acid dianhydride with a di-isocyanate to form a prepolymer which is then reacted with a difunctional compound having reactive hydrogen atoms. The resulting copolymer can be formed into high strength fiber or films.

Japanese 7229799 teaches a thermosetting resin containing an imide bond. The resin is produced by heating a linear polyurethane resin, obtained by reacting a polyisocyanate and a polyhidric alcohol with a polycarboxylic acid, its anhydride, mono-or di-alkyl esters or mixtures thereof, in an organic solvent. In an example diphenyl methane di-isocyanate and ethylene glycol and glycerine were reacted in a solvent to produce a polyurethane resin which was then reacted with trimellitic anhydride.

Japanese 4047278 teaches a colorless elastomer of copolyurethanes having amide or imide bonds. Diols of 400-6000 molecular weight are reacted with equimolar quantities of di-isocyanate to form a prepolymer which is then extended using compounds of the formula $(HO_2C)_2-R-(CO_2R_{1-2})$ or $(HO_2C)_2-R-CO_2R_1)$ where R, and $R_2$ are each equal to H, $CH_3$ $C_2$ $H_5$ or phenyl; and R is aliphatic if the di-isocyanate is aromatic or aromatic if the di-isocyanate is aliphatic, and imidizing the product. Preferred deals are polyethylene or polypropyleneglycol or polyesters.

German DT 2017511 teaches polyurethane elastomers with polyimide or polyamide acid structure for highly elastic filaments or films. Linear polyester can be reacted with excess di-isocyanate to form a prepolymer which is then reacted with a molar excess of aromatic or araliphatic diamine which is then polycondensed with a polyanhydride. The resulting polyamide acid is then cyclized at 50° to 300° C.

DESCRIPTION OF THE INVENTION

It has been discovered that polyurethane imide membranes can be used for the separation of aromatic hydrocarbons from mixtures of aromatic hydrocarbons and non-aromatic hydrocarbons by the selective permeation of the aromatic hydrocarbon through the membrane. The separation of aromatics from non-aromatics is useful in upgrading aromatics containing streams in petroleum refineries, such streams including, by way of example and not limitation, naphtha streams, heavy cat. naphtha streams, intermediate cat. naphtha streams, light aromatic streams boiling in the $C_5$–300° F. range, LCCO boiling in the 400°–650° F. range reformate streams and in chemical operations for the recovery of aromatics such as benzene, toluene, xylenes, etc.

The polyurethane imide membrane is prepared by casting using a solution of polyurethane imide copolymer or by using a solution of polyurethane amic acid polymer which is then chemically or thermally cyclized to the imide.

The polyurethane imide polymer is produced by reacting a dihydroxy or polyhydroxy compound with a di- or polyisocyanate to form a prepolymer which is then reacted with a di or poly anhydride or di or poly carboxylic acid. When using a di or polyanhydride the polyurethane imide is formed directly. When using the di- or poly carboxylic acid an amic acid intermediate is formed which must then be condensed to the imide.

The dihydroxy or polyhydroxy compounds can be any of the polyols, e.g. glycols such as polyethylene glycol, polypropylene glycol, etc. as well as polyesters or polyethers, and mixtures thereof. Polyesters and polyethers having molecular weights in the range of about 500 to 5000 can be used.

The polyester components are prepared from aliphatic or aromatic dicarboxylic acids and aliphatic or aromatic dialcohols. Aliphatic dicarboxylic acids refer to those materials having the general formula HOOCR- COOH where R contains 2 to 10 carbons (and may be either a straight or branched chain configuration). Aromatic dicarboxylic acids refer to those materials having the general structure HOOCRCOOH where R is:

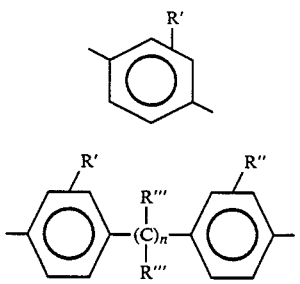

wherein R', R", and R''', may be the same or different and are selected from the group consisting of H and $C_1$-$C_5$ carbons or $C_6H_5$ and combinations thereof, and n is 0 to 4. It is to be understood that in the above formula each R' or R" may itself represent a mixture of H, $C_1$-$C_5$ or $C_6H_5$.

Dialcohols have the general structure HOROH where R may be

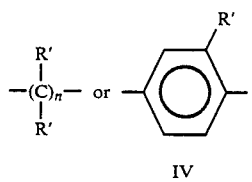

where n is 1 to 10, preferably 4 to 6, and R' is H, $C_1$ to $C_5$ or $C_6H_5$ or

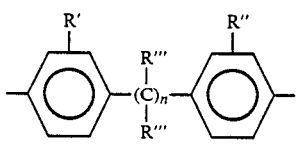

where R', R", R''' and n are defined in the same manner as for the aromatic dicarboxylic acids. An example of a useful dialcohol is bisphenol A.

The diisocyanates are preferably aromatic diisocyanates having the general structure:

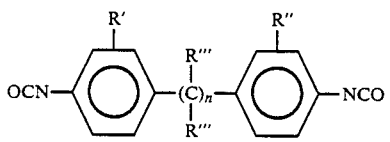

wherein R' and R" are the same or different and are selected from the group consisting of H, $C_1$-$C_5$ and $C_6H_5$ and mixtures thereof and n ranges from 0 to 4.

Aliphatic and cycloaliphatic di and poly isocyanates can also be used as can be mixtures of aliphatic, cycloaliphatic, aralkyl and aromatic polyisocyanates.

The chain extender used is one which produces the imide directly, e.g. di anhydrides or indirectly, e.g. di or poly carboxylic acids which produce amic acid groups which can be condensed/cyclized to the imide.

Any aromatic, aliphatic, cycloaliphatic or araliphatic dianhydride can be used. Examples of di anhydrides include by way of example and not limitation: Tetracarboxylic dianhydride, e.g. pyromellitic dianhydride, etc.

The dicarboxylic acid precursors of the dianhydrides can also be used, in which case an amic, acid is produced which must be thermally or chemically cyclized to the imide. In the case of the amide acid, the polyurethane amide acid in solution can be cast into a membrane and, in the form of a membrane, be chemically or thermally cyclized into the polyurethane imide polymer membrane.

Examples of the polyether polyols useful in the present invention as polymer precursors are poly ethylene glycols, (PEG), polypropylene glycol (PPG), polytetramethylene glycol, PEG/PPG random copolymers, etc. having molecular weight ranging from about 250 to 4000. Aliphatic diisocyanates which may be utilized are exemplified by hexamethylene diisocyanate (HDI), 1,6-diisocyanato-2,2,4,4-tetramethylhexane (TMDI), 1,4-cyclohexanyl diisocyanate (CHDI), isophorone diisocyanate (IPDI), while useful alkylaromatic diisocyanates are exemplified by toluene diisocyanate (TDI) and bitolylene diidocyanate (TODI). Aromatic diisocyanates are exemplified by 4,4,-diisocyanate diphenylemethane (MDI). Polyisocyanates are exemplified by polymeric MDI (PMDI) and carbodiimide modified MDI and isocyanurate isocyanates.

The above are presented solely by way of example. Those skilled in the art, with the present teaching before them, can select from the innumerable materials available the various starting materials which upon combination as described herein will produce a polyurethane imide copolymer which can then be cast into the membranes useful for the separation of aromatics from saturates.

The membranes are produced by preparing the corresponding polyurethane-imide or polyurethane amic acid in an appropriate solvent such as dimethylformamide.

The starting materials are combined in the order necessary to produce a polyurethane imide or polyurethane amic acid copolymer.

The copolymer in solvent is used as a casting solution. Polymer concentration in solvent ranges from 10 to 50 wt % preferably 15-30 wt % for casting dense films. When casting integral thin film composite membranes, e.g. thin layers of polymer on support backings such as porous polypropylene or porous teflon, preferably porous teflon the polymer concentration in solution is on the order of about 10% or less.

The casting solution is then poured or spread on an appropriate support medium, such as a metal or glass plate or, if desired, a woven fiber backing, such as woven fiber glass, nylon, polyester, etc. can be used if solvent removal during the casting sequence employs a vacuum, but preferably, non-woven backings such as thin films of porous polypropylene or porous teflon are employed. In general, however, backing materials used are those which are not attacked by the solvent(s) used to produce the copolymer casting solution.

When a polyurethane amic acid copolymer solution is used as the casting solution, the film of amic acid is cured in place to produce the polyurethaneimide upon chemical or thermal cyclization.

The membrane may be cast in any thickness, membranes ranging in thickness of from about 0.1 to about 50 microns being preferred.

Alternatively a very thin layer of the polyurethane imide copolymer can be deposited into a highly permeable, non-selective polyurethane layer producing a composite membrane comprising a thin dense layer of polyurethane imide membrane about 0.1 to 5 microns thick on a permeable, non-selective, thick polyurethane backing. The thick layer of polyurethane (about 20 to 100 microns thick) serves as a support layer permitting one to produce thin, dense, selective layers of polyurethane imide which would otherwise be mechanically unmanageable due to their thinness. Due to the chemical similarity between the polyurethane support layer and the polyurethane-imide selective layer, the two layers interact through hydrogen bonding to produce a very strong adhesion.

If one were to use this technique to produce sheet material, the thick, permeable polyurethane layer can be deposited on a suitable backing material such as porous fiber glass, polyethylene, polypropylene, nylon, teflon, etc. after which the thin, dense selective polyurethane imide layer would be deposited onto the polyurethane layer.

In producing hollow fibers or tubes using this composite membrane technique, first a tube or fiber of permeable polyurethane is produced after which a thin dense layer of the selective polyurethane imide material is deposited on either the outer or inner surface of the tube or fiber support.

The permeable polyurethane layer can be prepared from polyether glycols such as polypropylene glycol or polybutylene glycol plus aliphatic and/or aromatic diisocyanates (preferably aliphatic diisocyanates) using polyols (diols or triols) preferably aliphatic diols as chain extenders. Polyurethane membrane materials which satisfy the above requirement of permeability are the polyurethane membranes described in U.S. Pat. No. 4,115,465.

The membranes are useful for the separation of aromatics from non-aromatics in petroleum and chemical streams, and have been found to be particularly useful for the separation of larger, substituted aromatics from non-aromatics as are encountered in heavy cat naphtha streams. Other streams which are also suitable feed streams for aromatics from saturates separation are intermediate cat naphtha streams, (200°–320° F.) light aromatics content streams boiling in the $C_5$–300° F. range, light catalytic cycle oil boiling in the 400°–650° F. range, reformate streams as well as streams in chemical plants which contain recoverable quantities of benzene, toluene, xylene (BTX) or other aromatics in combination with saturates. The separation techniques which may successfully employ the membranes of the present invention include perstraction and pervaporation.

Perstraction involves the selective dissolution of particular components contained in a mixture into the membrane, the diffusion of those components through the membrane and the removal of the diffused components from the downstream side of the membrane by use of a liquid sweep stream. In the perstractive separation of aromatics from saturates in petroleum or chemical streams (particularly heavy cat naphtha streams) the aromatic molecules present in the feedstream dissolve into the membrane film due to similarities between the membrane solubility parameter and those of the aromatic species in the feed. The aromatics then permeate (diffuse) through the membrane and are swept away by a sweep liquid which is low in aromatics content. This keeps the concentration of aromatics at the permeate side of the membrane film low and maintains the concentration gradient which is responsible for the permeation of the aromatics through the membrane.

The sweep liquid is low in aromatics content so as not to itself decrease the concentration gradient. The sweep liquid is preferably a saturated hydrocarbon liquid with a boiling point much lower or much higher than that of the permeated aromatics. This is to facilitate separation, as by simple distillation. Suitable sweep liquids, therefor, would include, for example, $C_3$ to $C_6$ saturated hydrocarbons and lube basestocks ($C_{15}$–$C_{20}$).

The perstraction process is run at any convenient temperature, preferably as low as possible.

The choice of pressure is not critical since the perstraction process is not dependent on pressure, but on the ability of the aromatic components in the feed to dissolve into and migrate through the membrane under a concentration driving force. Consequently, any convenient pressure may be employed, the lower the better to avoid undesirable compaction, if the membrane is supported on a porous backing, or rupture of the membrane, if it is not.

If $C_3$ or $C_4$ sweep liquids are used at 25° C. or above in liquid state, the pressure must be increased to keep them in the liquid phase.

Pervaporation, by comparison, is run at generally higher temperatures than perstraction and relies on vacuum on the permeate side to evaporate the permeate from the surface of the membrane and maintain the concentration gradient driving force which drives the separation process. As in perstraction, the aromatic molecules present in the feed dissolve into the membrane film, migrate through said film and reemerge on the permeate side under the influence of a concentration gradient. Pervaporative separation of aromatics from saturates can be performed at a temperature of about 25° C. for the separation of benzene from hexane but for separation of heavier aromatic/saturate mixtures, such as heavy cat naphtha, higher temperatures of at least 80° C. and higher, preferably at least 100° C. and higher, more preferably 120° C. and higher (up to about 170° to 200° C.) can be used, the maximum upper limit being that temperature at which the membrane is physically damaged. Vacuum on the order of 1-50 mm Hg is pulled on the permeate side. The vacuum stream containing the permeate is cooled to condense out the highly aromatic permeate. Condensation temperature should be below the dew point of the permeate at a given vacuum level.

The membrane itself may be in any convenient form utilizing any convenient module design. Thus, sheets of membrane material may be used in spiral wound or plate and frame permeation cell modules. Tubes and hollow fibers of membranes may be used in bundled configurations with either the feed or the sweep liquid (or vacuum) in the internal space of the tube or fiber, the other material obviously being on the other side.

Most conveniently, the membrane is used in a hollow fiber configuration with the feed introduced on the exterior side of the fiber, the sweep liquid flowing on the inside of the hollow fiber to sweep away the permeated highly aromatic species, thereby maintaining the desired concentration gradient. The sweep liquid, along with aromatics contained therein, is passed to separation means, typically distillation means, however, if a sweep liquid of low enough molecular weight is used, such as liquefied propane or butane, the sweep liquid can be permitted to simply evaporate, the liquid aromatics being recovered and the gaseous propane or butane (for example) being recovered and reliquefied by application of pressure or lowering the temperature.

The present invention will be better understood by reference to the following Examples which are offered by way of illustration and not limitation.

EXAMPLE 1

A solution of polyurethane-imide is prepared by adding fourteen point eight (14.8) grams (0.0072 moles) of polyethylene adipate (2000 MW) and three point six (3.6) grams (0.014 moles) of 4,4 - diphenylmethane diisocyanate to a 250 ml flask equipped with a stirrer and drying tube. The temperature is increased to 90° C. and maintained for 2 hours while stirring, producing an isocyanate-capped-prepolymer. Ten milliliters of distilled dimethylformamide is added to the prepolymer and stirred until a clear solution results. One point six (1.6) grams (0.0072 moles) of 1,2,4,5-benzenetetracarboxylic anhydride (PMDA) (10 grams of which was rinsed with 23 milliliters of acetone to remove impurities, vacuum filtered and air dried under vacuum for 2 hours at room temperature) is added as a chain extender to the prepolymer mixture. The use of commercially available high purity PMDA would make this wash step unnecessary. The solution was then stirred for 120 min. at a temperature of 85° C. Another 20 ml of dimethylformamide was added to the solution and stirred until thoroughly mixed. After cooling the solution to room temperature, films were cast on a glass plate using a 5 mil casting knife and placed in a convection oven at 150° C. for 90 min. to complete the formation of the imide groups.

Runs 238a and 238b, summarized in Table 1, clearly demonstrate that the polyurethane-imide membranes are stable in HCN at temperatures above 100° C. Permeabilities greater than 2000 kg-u/m²-d were obtained, indicating the large potential for thin film versions. It is understood that although the data shown were obtained for a pervaporation operation, these membranes would also be effective in perstraction or any other membrane separation process.

TABLE 1

HEAVY CAT NAPHTHA: 51 VOL % AROMATICS, PERVAPORATION @ 5 MBAR VACUUM

| Run # | Temp. °C. | Permeate Aromatics[1] (vol %) | Selectivity[2] | Flux kg/m²·day | Permeability kg·u/m²·day |
|---|---|---|---|---|---|
| 238a | 140 | 84 | 5.1 | 122 | 2400 |
| 238b | 150 | 84 | 5.1 | 148 | 3000 |

[1]Based on refractive index (RI) correlation for Dartmouth HCN Vol % Aromatics = 807.99 × RI - 1126.24

[2]Defined as $$\frac{\frac{Aromatics}{[Non-Aromatics]} permeate}{\frac{Aromatics}{[Non-Aromatics]} feed}$$

EXAMPLE 2

A solution of polyurethane imide is prepared by dehydrating thirty-six point eight (36.8) grams (0.018 moles) of polyethylene adipate (2000 MW) at 100C under 2 to 3 mbar vacuum for 1 hour. Nine point two (9.2) grams (0.036 moles) of 4,4-diphenylmethane diisocyanate is added and the mixture is stirred for 2 hours at 90–95C. with stirring under a nitrogen atmosphere. This produces an isocyanate capped prepolymer. Four point zero (4.0) grams (0.018 moles) of 1,2,4,5-benzenetetracarboxylic anhydride (of which ten grams was rinsed with twenty-five milliliters of acetone, vacuum filtered and dried under vacuum for 2 hours at room temperature) was dissolved in thirty grams of distilled dimethylformamide and added as a chain extender to the prepolymer mixture. This solution was then stirred for 90 min. at 65° C. under a nitrogen atmosphere. After cooling to room temperature films were cast on a glass plate using a 15 mil casting knife and placed in convection oven at 120° C. for one hour. The films were then further heat treated at 190°–200° C. for 2 hours to complete the formation of the imide groups.

Heavy Cat Naphtha: 51 vol % aromatics.
Pervaporation at 10 mbar vacuum.

| Run # | Temp. °C. | Permeate Aromatics | Selectivity | Flux kg/m²·day | Permeability kg·u/m²·day |
|---|---|---|---|---|---|
| 372A | 140 | 88 | 7.0 | 36 | 2700 |
| 372b | 160 | 88 | 7.0 | 66 | 4950 |

The permeate aromatics and selectivity definitions are the same as in Table 1.

EXAMPLE 3

For this example the same polymer preparation procedure and formulation was used as for example 2 but eliminated the prepolymer step. The 1,2,4,5 - Benzenetetracarboxylic anhydride, was dissolved in 40 ml of distilled dimethylformamide (DMF) and mixed with the polyethylene adipate and 4,4 - diphenylmethane diisocyanate. This mixture was stirred under a nitrogen atmosphere at 65°–70° C. for 30 min. The temperature was raised to 90° C. for an additional 2.5 hours to complete the formation of polyurethane-imide polymer. This is known as the "one shot approach" compared to the prepolymer method. The mixture was diluted with DMF to a concentration of 20% wt. After storing the solution at 20°–22° C. for 12 hours, 0.5% wt. Zonyl FSN fluorosurfactant (supplied by Dupont) was added and thoroughly mixed into the polymer solution. Using a Teflon membrane (K-150 supplied by Desalination Systems) as a support, the PUI polymer was solution coated onto the Teflon membrane and oven dried at 185°–190° C. for 1 hour. This resulted in the formation of a thin-film composite membrane.

TABLE 3

Heavy Cat Naphtha: 51 vol % Aromatics.
Pervaporation @ 10 mbar vacuum.

| Run # | Temp. °C. | Flux kg/m²·day | Permeate % Aromatics | Selectivity |
|---|---|---|---|---|
| 384 | 140 | 170 | 86 | 5.9 |

Permeate Aromatics and Selectivity definitions same as in Table 1.

What is claimed is:

1. A method for separating aromatic hydrocarbons from a mixture containing said aromatic hydrocarbons in combination with non-aromatic hydrocarbons, the method comprising contacting said mixture under appropriate separation conditions with a membrane comprising a polyurethane-imide membrane to thereby selectively permeate the aromatic hydrocarbon through the membrane.

2. The method of claim 1 wherein the separation is conducted under reverse osmosis, dialysis, pervaporation or perstraction conditions.

3. The method of claim 1 wherein the separation is conducted under pervaporation or perstraction conditions.

4. The method of claim 3 wherein the separation is conducted under pervaporation conditions.

5. The method of claim 1 or 4 wherein the polyurethane-imide membrane is supported on a backing.

6. The method of claim 5 wherein the backing is teflon or polypropylene.

7. The method of claim 6 wherein the backing is teflon.

8. The method of claim 1 wherein the mixture containing aromatics and non-aromatics which is contacted with the polyurethane-imide membrane is selected from cat naphtha, heavy cat naphtha, light aromatics content streams boiling in the $C_5$–300° F. range, light catalytic cycle oil boiling in the 400°–650° F. range, reformate streams, and streams containing recoverable quantities of benzene, toluene and xylene.

9. The method of claim 4 wherein the pervaporation process is performed at a temperature up to about 200° C. and at a vacuum on the order of 1 to 50 mm Hg on the permeate side of the membrane.

10. The method of claim 7 wherein the pervaporation process is performed at a temperature up to about 200° C. and at a vacuum on the order of 1 to 50 mm Hg on the permeate side of the membrane.

* * * * *